(12) United States Patent
Brendel et al.

(10) Patent No.: US 9,760,992 B2
(45) Date of Patent: Sep. 12, 2017

(54) MOTION COMPENSATED ITERATIVE RECONSTRUCTION

(71) Applicant: KONINKLIJKE PHILIPS N.V., Eindhoven (NL)

(72) Inventors: Bernhard Johannes Brendel, Norderstedt (DE); Thomas Koehler, Norderstedt (DE); Rolf Dieter Bippus, Hamburg (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/917,093

(22) PCT Filed: Sep. 17, 2014

(86) PCT No.: PCT/IB2014/064578
§ 371 (c)(1),
(2) Date: Mar. 7, 2016

(87) PCT Pub. No.: WO2015/044837
PCT Pub. Date: Apr. 2, 2015

(65) Prior Publication Data
US 2016/0210741 A1    Jul. 21, 2016

Related U.S. Application Data

(60) Provisional application No. 61/883,415, filed on Sep. 27, 2013.

(51) Int. Cl.
*G06K 9/40*    (2006.01)
*G06T 7/00*    (2017.01)
(Continued)

(52) U.S. Cl.
CPC ............ *G06T 7/0012* (2013.01); *A61B 6/032* (2013.01); *A61B 6/5264* (2013.01);
(Continued)

(58) Field of Classification Search
None
See application file for complete search history.

(56) References Cited

U.S. PATENT DOCUMENTS 6,934,357 B2 *    8/2005    Boyd ..................... A61B 6/032
378/62
7,221,728 B2 *    5/2007    Edic ....................... A61B 6/032
378/4
(Continued)

OTHER PUBLICATIONS

Kybic, "Multiresolution spline warping for EPI registration," Proc. SPIE 3813, Wavelet Application in Signal and Image Processing VII, 571 (Oct. 26, 1999).*
(Continued)

*Primary Examiner* — Feng Niu

(57) ABSTRACT

A method includes re-sampling current image data representing a reference motion state into a plurality of different groups, each group corresponding to a different motion state of moving tissue of interest, forward projecting each of the plurality of groups, generating a plurality of groups of forward projected data, each group of forward projected data corresponding to a group of the re-sampled current image data, determining update projection data based on a comparison between the forward projected data and the measured projection data, grouping the update projection data into a plurality of groups, each group corresponding to a different motion state of the moving tissue of interest, back projecting each of the plurality of groups, generating a plurality of groups of update image data, re-sampling each group of update image data to the reference motion state of the current image, and generating new current image data based on the current image data and the re-sampled update image data.

21 Claims, 5 Drawing Sheets

Figure 1:
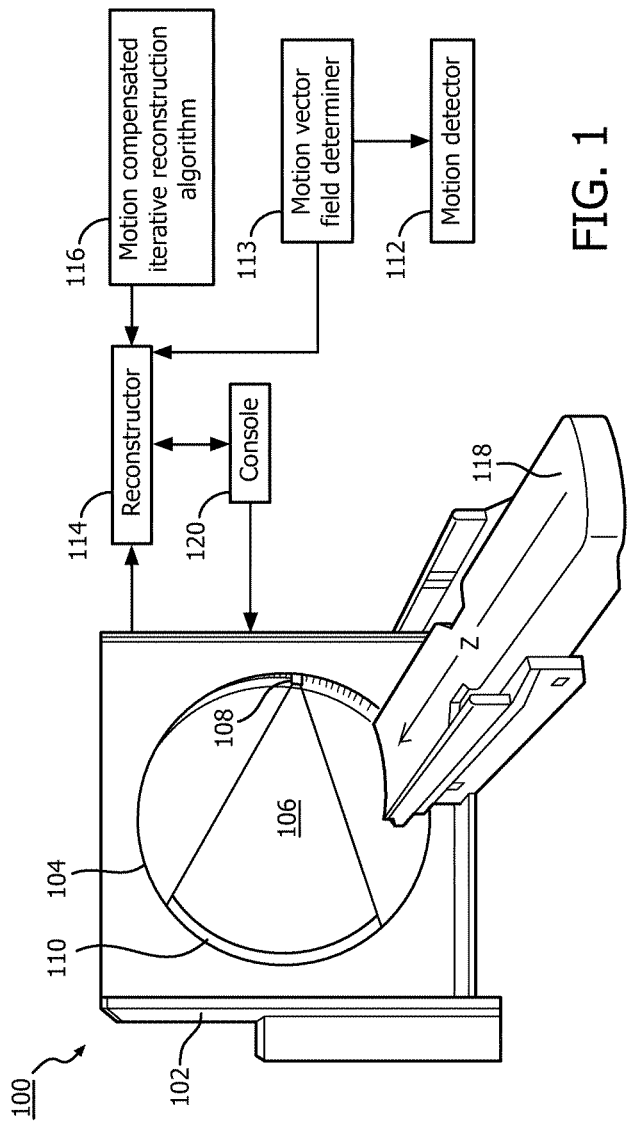

(51) Int. Cl.
  G06T 11/00    (2006.01)
  A61B 6/03     (2006.01)
  A61B 6/00     (2006.01)
  G06K 9/62     (2006.01)
  G06T 1/20     (2006.01)
  G06T 11/60    (2006.01)
  G06T 7/246    (2017.01)

(52) U.S. Cl.
  CPC .............. *G06K 9/6202* (2013.01); *G06T 1/20* (2013.01); *G06T 7/246* (2017.01); *G06T 11/006* (2013.01); *G06T 11/60* (2013.01); *G06T 2207/10081* (2013.01); *G06T 2211/412* (2013.01); *G06T 2211/421* (2013.01); *G06T 2211/424* (2013.01)

(56) References Cited

U.S. PATENT DOCUMENTS

| | | | |
|---|---|---|---|
| 7,426,256 B2 | 9/2008 | Rasche | |
| 7,599,540 B2* | 10/2009 | Koehler | G06T 11/006 378/21 |
| 8,306,121 B2 | 11/2012 | Jia | |
| 2003/0113002 A1* | 6/2003 | Philomin | G06K 9/00885 382/116 |
| 2004/0136490 A1* | 7/2004 | Edic | A61B 6/032 378/4 |
| 2004/0136501 A1* | 7/2004 | Boyd | A61B 6/032 378/210 |
| 2006/0140482 A1* | 6/2006 | Koehler | G06T 11/006 382/193 |
| 2012/0134586 A1* | 5/2012 | Pajaniradja | G06K 9/00986 382/170 |
| 2013/0034163 A1 | 2/2013 | Amonou | |

OTHER PUBLICATIONS

Isola, et al., "Motion-compensated iterative cone-beam CT image reconstruction with adapted blobs as basis functions", Phys. Med. Biol. 53, (2008).

Isola, et al., "Motion compensated iterative reconstruction of a region of interest in cardiac cone-beam CT", Computerized Medical Imaging and Graphics, Pergamon Press, vol. 34, No. 2, Mar. 2010.

Van Stevendaal, et al., "A Motion-compensated scheme for helical cone-beam reconstructions in cardiac CT angiography", Med. Phys. 35, Jul. 2008

* cited by examiner

MOTION COMPENSATED ITERATIVE RECONSTRUCTION

CROSS REFERENCE TO RELATED APPLICATIONS

This application is the U.S. National Phase application under 35 U.S.C. §371 of International Application No. PCT/IB2014/064578, filed Sep. 17, 2014, published as WO 2015/044837 on Apr. 2, 2015, which claims the benefit of U.S. Provisional Patent Application No. 61/883,415 filed Sep. 27, 2013 . These applications are hereby incorporated by reference herein.

The following generally relates to reconstruction and more particularly to motion compensated iterative reconstruction and is described with particular application to computed tomography (CT); however, the following is also amenable to other imaging modalities such as positron emission tomography (PET), single photon emission computed tomography (SPECT) and/or other imaging modality.

A CT scanner generally includes an x-ray tube mounted on a rotatable gantry opposite a detector array located across an examination region. The rotatable gantry, and hence the x-ray tube, rotates around the examination region, and the x-ray tube emits radiation that traverses the examination region and a portion of a subject therein. The detector array detects the radiation and generates projection data indicative thereof. A reconstructor reconstructs the projection data, generating volumetric image data, which can be processed to generate one or more images.

Reconstruction algorithms have included non-iterative reconstruction algorithms such as filtered back projection (FBP) and iterative reconstruction algorithms such as algebraic and statistical based reconstruction algorithms. Iterative reconstruction algorithms may reduce the dose required for a given image quality as compared to a conventional FBP reconstruction algorithm. Unfortunately, iterative reconstruction algorithms have been computationally costly, requiring more reconstruction time relative to FBP reconstruction algorithm. This prohibited the usage of iterative reconstruction in a clinical setting for many years. Only recently with modern hardware and massive parallelization it was possible to achieve reconstruction times allowing to utilize iterative reconstruction for selected applications in a clinical setting.

Motion compensated reconstruction (MCR) algorithms have been used to reduce blurring in reconstructed images caused by motion, for example, for cardiac and/or other applications. One approach has been to estimate the motion between different motion-states of the heart based on FBP reconstructions of low quality, and use this information to generate improved FBP images in a second pass reconstruction. The estimated motion is commonly represented as a set of motion vector fields (MVFs) describing the movement of each image voxel from a reference heart phase to a number of other heart phases. The MVF is applied during back-projection to determine for each projection the voxels that have been in the according rays. This approach improves image quality.

Isola et al., "Motion-compensated iterative cone-beam CT image reconstruction with adapted blobs as basis functions", Phys. Med. Biol. 53, pp. 6777 (2008), describes an approach which combines motion compensation with iterative reconstruction, which allows for both dose reduction and reduced image blurring, concurrently. With this approach, motion vector fields are incorporated into the iterative reconstruction by modifying voxel position, size and shape for each heart phase differently. Unfortunately, projections based on a volume in which the voxels are no longer positioned on a regular grid, and in which voxels have different sizes and shapes, increase the reconstruction time significantly, complicating the utilization in a clinical setting considerably.

Aspects described herein address the above-referenced problems and others.

The following describes an approach that combines iterative reconstruction (IR) and motion compensated reconstruction (MCR) by incorporating motion vector fields (MVFs) into the iterative reconstruction via re-sampling the image data in a manner in which the position and geometry of the voxels (e.g., size, shape, etc.) representing the volume data during forward- and back-projection are kept on a regular grid, independent from the MVF. In one instance, this allows for parallel processing and shortening reconstruction time relative to a configuration in which voxel position and geometry is changed.

In one aspect, a method includes re-sampling current image data representing a reference motion state into a plurality of different groups. Each group corresponding to a different motion state of moving tissue of interest. The method further includes forward projecting each of the plurality of groups. The method further includes generating a plurality of groups of forward projected data. Each group of forward projected data corresponds to a group of the re-sampled current image data. The method further includes determining update projection data based on a comparison between the forward projected data and the measured projection data. The method further includes grouping the update projection data into a plurality of different groups. Each group corresponding to a different motion state of the moving tissue of interest. The method further includes back projecting each of the plurality of groups. The method further includes generating a plurality of groups of update image data. The method further includes re-sampling each group of update image data to reference motion state of the current image. The method further includes generating new current image data by combining the current image data and each of the groups of re-sampled update image data.

In another aspect, an image system includes a source that emits radiation, a detector array that detects radiation and generates projection data indicative thereof, and a reconstructor that reconstructs the projection data using a motion compensated iterative reconstruction algorithm in which forward projections and back projections are performed on image volumes represented by voxels on a regular grid through resampling and generates volumetric image data.

In another aspect, a computer readable storage medium is encoded with computer readable instructions, which, when executed by a processer, causes the processor to: re-sample current image data into a plurality of different groups corresponding to different motion states of moving tissue of interest using a plurality of different motion vector fields that indicate a displacement of tissue in a reference state of the current image data to the corresponding different motion states, forward project each of the plurality of groups, generating a plurality of groups of forward projected data, each group of forward projected data corresponding to a group of the re-sampled current image data, determine update projection data based on a comparison between the forward projected data and the measured projection data, group the update projection data into a plurality of different groups, each group corresponding to a different motion state of the moving tissue of interest, back project each of the plurality of groups, generating a plurality of groups of update image data, re-sample each group of update image data to the reference state of the current image, generate new current image data by combining the current image data and each of the groups of re-sampled update image data, and repeat, at least one more time, all of the above acts, but with the new current image data in place of the current image data.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system with a reconstructor that employs a motion compensated iterative reconstruction algorithm.

Figure 2:
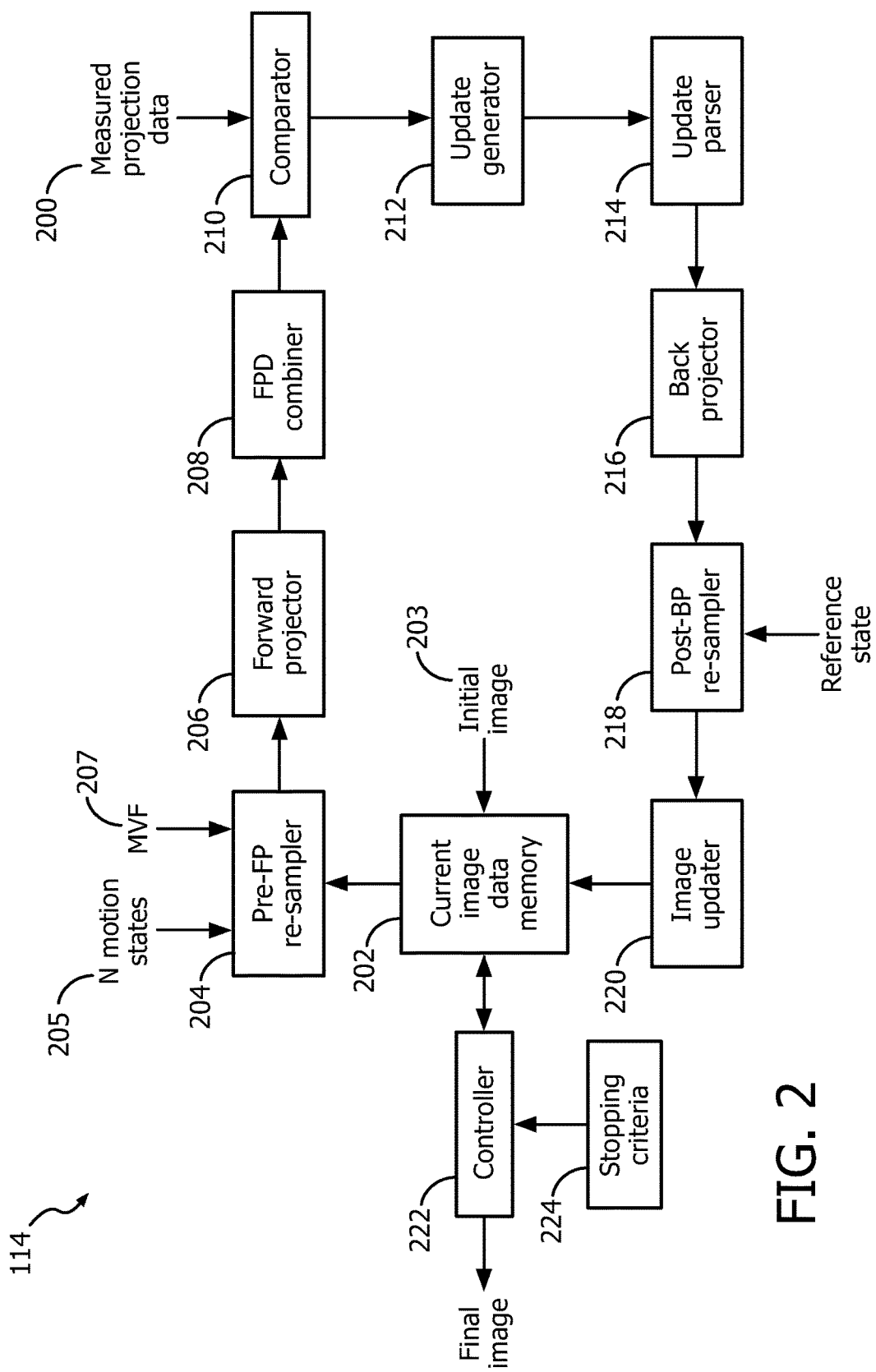

FIG. 2 schematically illustrates an example of the reconstructor of FIG. 1.

Figure 3:
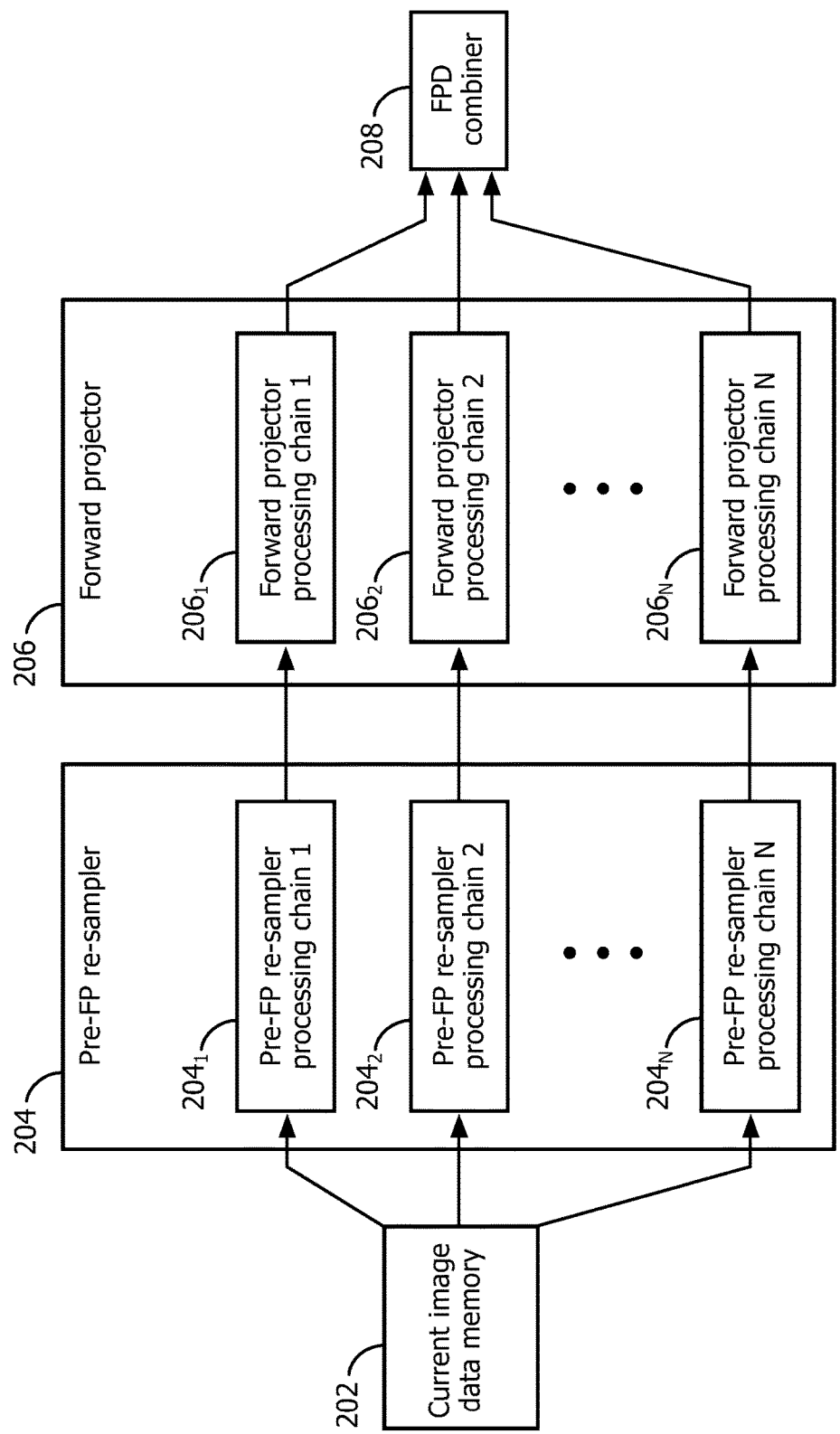

FIG. 3 schematically illustrates a portion of the re-sampling and forward projection processing chains of the reconstructor of FIG. 2.

Figure 4:
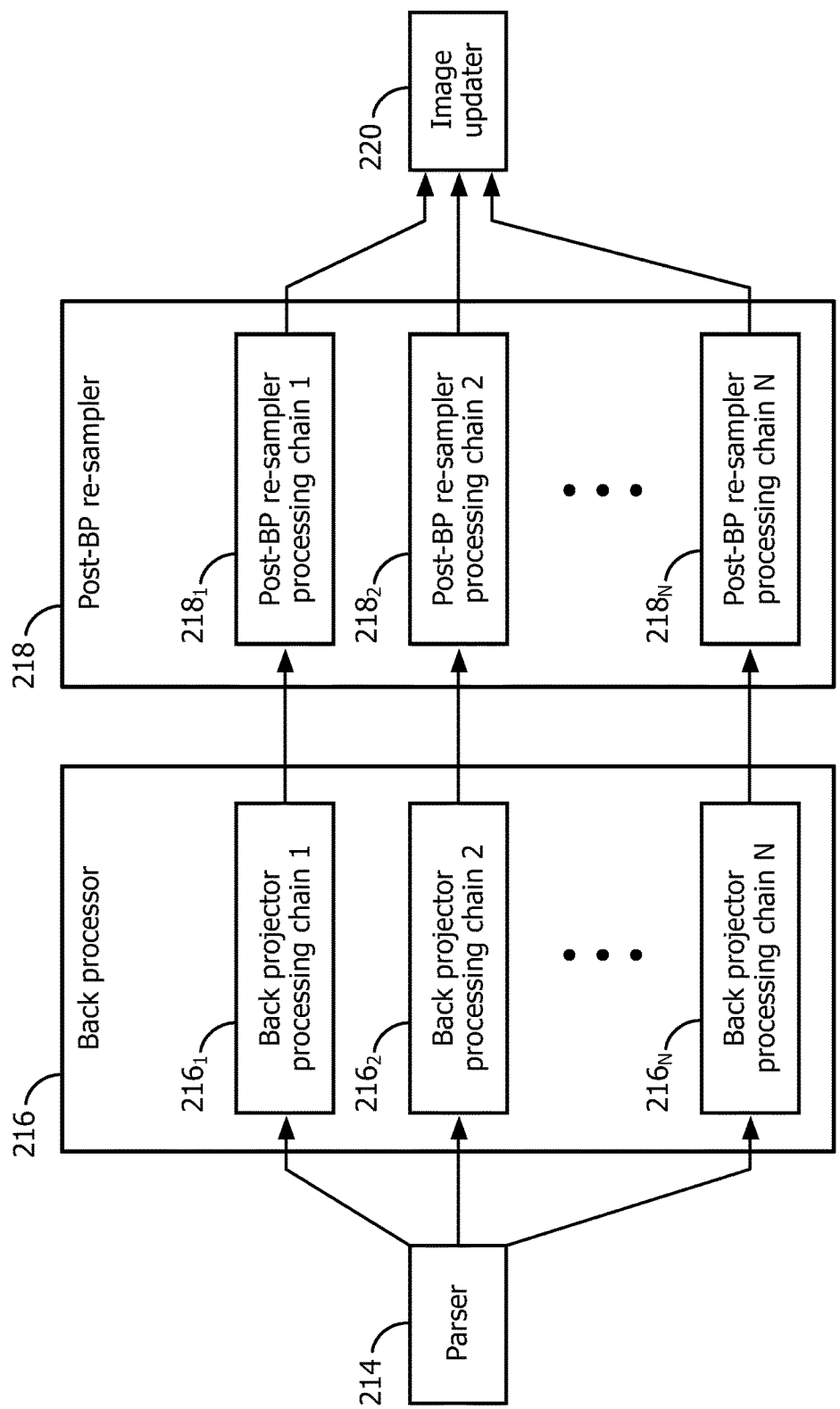

FIG. 4 schematically illustrates a portion of the back projection and re-sampling processing chains of the reconstructor of FIG. 2.

Figure 5:
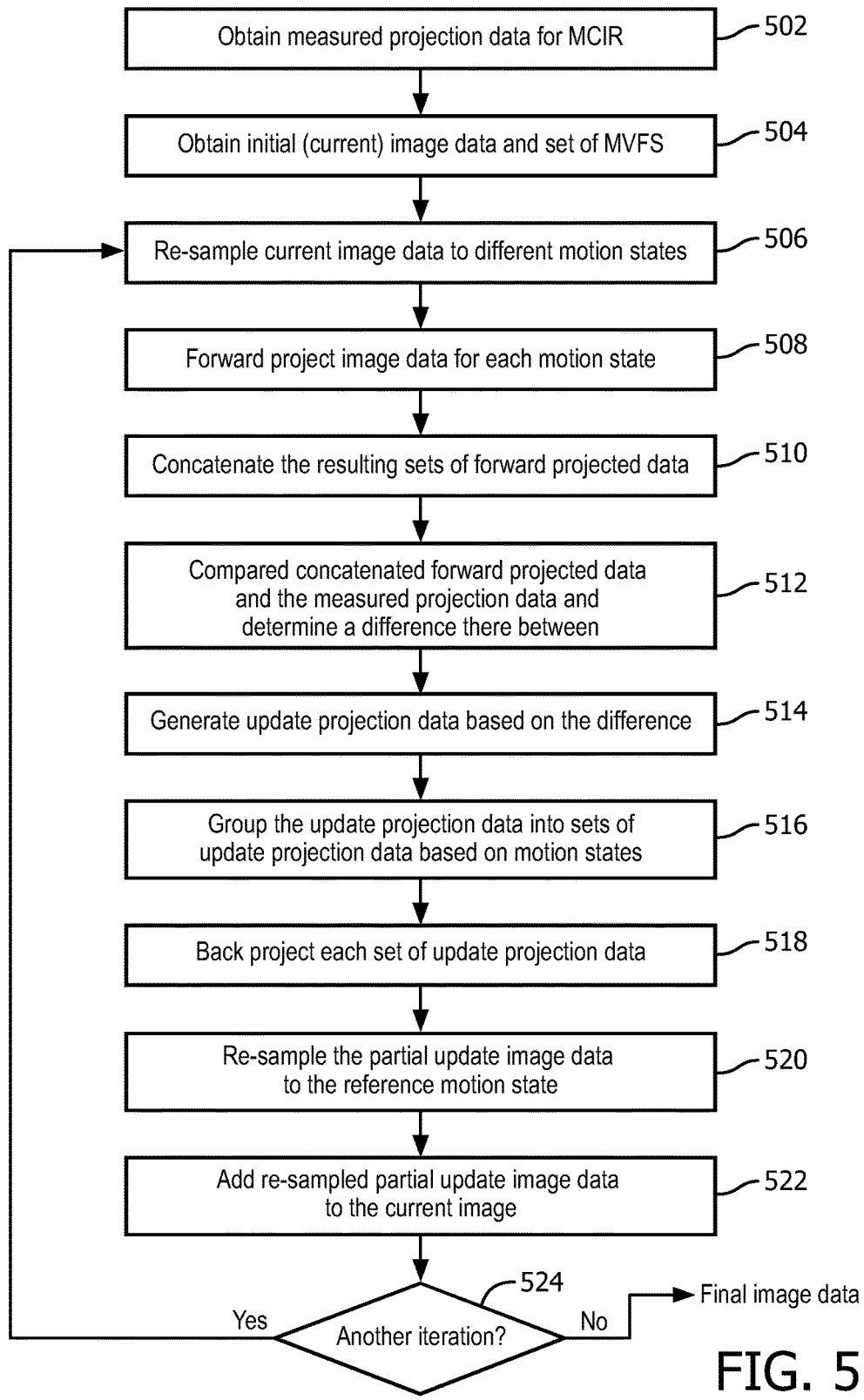

FIG. 5 illustrates an example method for motion compensated iterative reconstruction.

FIG. 1 illustrates an imaging system 100 such as a computed tomography (CT) scanner. In another embodiments, the imaging system 100 includes as positron emission tomography (PET), single photon emission computed tomography (SPECT) and/or other scanner. The illustrated imaging system 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by the rotating gantry 104 and rotates with the rotating gantry 104 about the examination region 106, and emits radiation that traverses the examination region 106. A one or two dimensional radiation sensitive detector array 110, located opposite the radiation source 108 across the examination region 106, includes a plurality of detector pixels that detect radiation traversing the examination region 106 and generate projection data indicative thereof.

A motion detector 112 detects motion of moving tissue of a subject during an imaging acquisition and generates a motion signal indicative thereof. Examples of moving tissue include lung tissue, heart tissue, and/or other tissue. The motion detector 112 may include at least one of a respiratory belt, light emitting landmarks, an ECG monitor, etc. The motion signal is mapped to data acquisition. This can be achieved through time stamps, including information about the motion signal in the header file of the acquired data, and/or otherwise.

A motion vector field determiner 113 determines a set of motion vector fields (MVFs) based on the motion signal for one or more sub-sets of motion states. Generally, a MVF maps a position of tissue between images or slices of the volumetric image data, thereby describing the motion of the tissue from one image to another image. In this example, the set of MVFs corresponds to N time points or motion states, where N is an integer, e.g., in the order of three (3) to twenty (20), such as five (5) to ten (10) or other number of time points.

The following provides a non-limiting example for determining N. For a heart rate of x beats per second and a rotation speed of one (1) revolution per y seconds, (y/x) % of the heart cycle is covered each revolution. For one (1) MVF every z % of a heart beat (e.g., as determined from the R-peaks of the QRS complex of an ECG signal), N=(y/x)/z. For example, where x=1, y=0.250 seconds, and z=5%, N=(0.250/1×100)/5%=5. It is to be understood that this example is provided for explanatory purposes and is not limiting. Generally, N will increase with increased heart rate and decrease with decreased hear rate.

A reconstructor 114 reconstructs the projection data and generates volumetric image data indicative of the examination region 106. The illustrated reconstructor 114 is configured to utilize, at least, a motion compensated iterative reconstruction algorithm 116. With a non-motion compensated iterative reconstruction algorithm, a current image (i.e., voxels) is forward projected producing estimated or intermediate projection data, which is compared with measured projection data, and an update is generated based on the comparison there between, and the current image is updated based on the update, producing a new current image. The above is repeated one or more times until predetermined stopping criteria is satisfied.

As described in greater detail below, the reconstructor 114 includes one or more computer processors, which, in response to executing the motion compensated iterative reconstruction algorithm 116, incorporates the motion vector fields into the current image before forward projecting the current image and into the image update before combining the update with the current image. The following is achieved without modifying voxel position, size and shape such that the voxels are no longer positioned on a regular grid and have different size and shape. In contrast, all voxels have equal size, with a same x, y and z distances, and remain on a cubic grid, which reduces computation time relative to a configuration in which voxel position, size and shape are different.

A support 118, such as a couch, supports a subject in the examination region 106 and can be used to position the subject with respect to x, y, and/or z axes before, during and/or after scanning. A computing system serves as an operator console 120, and includes an output device such as a display and an input device such as a keyboard, mouse, and/or the like. Software resident on the console 120 allows the operator to control the operation of the system 100, e.g., identifying a reconstruction algorithm, etc.

Turning to FIG. 2, an example of the reconstructor 114 is schematically illustrated.

Measured projection data 200 is received to reconstruct. The measured projection data 200 can be from the imaging system 100, other imaging system, and/or a data repository. Current image data memory 202 stores the current image data. For the first iteration, the current image data includes an initial image 203, which may be all zeros, an atlas image, a conventionally reconstructed image (e.g., FBP), and/or other image. For each subsequent iteration, the current image data is the image data processed in the previous iteration plus the image data update generated based thereon.

A pre-forward projection (FP) re-sampler 204 receives the current image data from the current image data memory 202, the N motion states 205, and the MVFs 207 for the N motion states 205. The pre-FP re-sampler 204 re-samples the current image data to each of the N motion states 205 by applying respective MVFs 207. The resampled images are represented on a regular grid, e.g. by a same geometry grid of voxels as the current image. A forward projector 206 forward projects each of the N sets of re-sampled image data, generating, for each set of the image data and thus each of the N motion states 205, all projections belonging to that set. After the resampling and forward projection, a complete forward projection dataset is produced.

Each of the pre-FP re-sampler 204 and the forward projector 206, in the illustrated embodiment, processes data in parallel. This can be achieved through a graphics processing unit(s), or GPU, and/or other processor. The parallelization can be achieved by parallelization within the forward projection of one of the resampled images, which is easy to implement since voxels are placed on a regular grid, and/or by parallelization of multiple forward projections of different resampled images. The second case is illustrated in FIG. 3, which shows an example in which the pre-FP re-sampler 204 includes N processing chains $204_1$, $204_2$, ..., $204_N$, and the forward projector 206 includes N processing chains $206_1$, $206_2$, ..., $206_N$. Each processing chain pair $204_1/206_1$, $204_2/206_2$, ..., $204_N/206_N$ processes a corresponding one of the N sets of current image data. Returning to FIG. 2, forward projected data (FPD) combiner 208 combines the projections for the individual motion states. In one instance, this includes concatenating the forward projected data. In a variation, the pre-FP re-sampler 204 and/or the forward projector 206 process the data in series. In another variation, the pre-FP re-sampler 204 and/or the forward projector 206 processes sub-portions of the data in parallel and different sub-portions of the data in series.

A comparator 210 compares the concatenated forward projected projection data with the measured projection data 200, which again, may be the projection data generated by the imaging system 100 and/or other imaging system, generating a difference signal, indicative of a discrepancy between the forward projected projection data and the measured projection data 200. An update generator 212 generates update projection data based on the difference signal, which is data predicted to decrease the discrepancy between the forward projected data and the measured projection data 200. An update parser 214 parses the update projection data into N sets of update projection data, each set corresponding to one of the N motion states 205.

A back projector 216 back projects each of the N sets of update projection data, generating N sets of update image data, each set corresponding to one of the N motion states 205. A post-back projection (BP) re-sampler 218 receives the N sets of update image data and the motion state of the current image data (reference state), and re-samples each of the N sets from the motion state it represents to the reference motion state, which is the motion state of the current image, based on the MVF's. The post BP re-sampler 218 re-samples the N sets of update image data to of the reference motion state by applying respective MVF's of the MVFs 207. The resampled N sets of image data are represented in the geometry grid of voxels as the current image.

Each of the back projector 216 and the post BP re-sampler 218, in the illustrated embodiment, processes data in parallel. This can be achieved through a graphics processing unit(s), or GPU, and/or other processor. FIG. 4 shows an example in which the back projector 216 includes N processing chains $216_1$, $216_2$, ..., $216_N$, and the post BP re-sampler 218 includes N processing chains $218_1$, $218_2$, ..., $218_N$. Each processing chain pair $216_1/218_1$, $216_2/218_2$, ..., $216_N/218_N$ processes a corresponding one of the N sets of update data. Returning to FIG. 2, an image updater 220 updates the current image data in the current image data memory 202, generating new current image data. In one non-limiting instance, this includes adding the individual N re-sampled sets of update image data to the current image data in the current image data memory 202.

The pre-FP re-sampler 204 and the post BP re-sampler 218 can be variously implemented. This includes as separate re-samplers or a same re-sampler. An example of a suitable re-sampling includes the re-sampling discussed in Kybic, "Multiresolution spline warping for EPI registration," Proc. SPIE 3813, Wavelet Application in Signal and Image Processing VII, 571 (Oct. 26, 1999). This reference discusses warping an input image to an output image based on a MVF. Other re-sampling approaches are also contemplated herein.

For each subsequent iteration, the new current image data in the current image data memory 202, which is generated from processing the current image data in the current image data memory 202, is processed. A controller 222 controls the number of iterations based on predetermined stopping criteria 224. Examples of suitable stopping criteria 224 includes a predetermined number of iterations, an elapsed amount of time, an error threshold between the forward projected data and the measured projection data, and/or other stopping criteria. The controller 222 outputs final image data in response to the stopping criteria 224 being satisfied, the final image data being the present current image data in the current image data memory 202.

FIG. 5 illustrates example method of a motion compensated iterative reconstruction.

It is to be appreciated that the ordering of the acts of these methods is not limiting. As such, other orderings are contemplated herein. In addition, one or more acts may be omitted and/or one or more additional acts may be included.

At 502, measured projection data is obtained for motion compensated iterative reconstruction (MCIR).

At 504, initial (current) image data and a set of MVFs for a corresponding set of motion states of interest are obtained, and the initial image data is stored as current image data.

At 506, the current image data is re-sampled into a plurality of sets of image data, each set corresponding to one of the motion states, and the resulting voxels have a geometry (size and shape) and position on a regular grid, e.g. that of the initial image data.

At 508, each of the plurality of sets of the image data is forward projected, creating a plurality of sets of forward projected data, each set corresponding to a particular motion state, with all of the sets of forward projected data, collectively, covering all of the motion states.

At 510, the sets of forward projected data are concatenated.

At 512, the concatenated projection data is compared with the measured projection data and a difference signal there between is determined.

At 514, update projection data is generated based on the difference signal.

At 516, the update projection data is grouped based on the set of motion states.

At 518, each set of the updated projection data is back projected, generating sets of partial update image data.

At 520, the sets of partial update image data are re-sampled back into the reference motion state.

At 522, the re-sampled partial update image data is added to the current image data, producing new current image data.

At 524, if another iteration is to be performed, then acts 506-524 are repeated one or more times, with the current image data being the new current image data. This is achieved by determining whether stopping criteria has been satisfied. As discussed herein, examples of suitable stopping criteria include a predetermined number of iterations, an elapsed amount of time, an error threshold between the forward projected data and the measured projection data, and/or other stopping criteria. At 524, if another iteration is not to be performed, then final image data is output.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for reconstructing measured projection data using a motion compensated iterative reconstruction algorithm and generating reconstructed image data, comprising:
re-sampling current image data representing a reference motion state into a plurality of groups of image data, each group of image data corresponding to a different motion state of a moving tissue of interest, wherein re-sampling the current image data comprises applying a corresponding motion vector field of a set of motion vector fields to the current image data for each group of the plurality of groups of image data, wherein each motion vector field of the set of motion vector fields corresponds to the different motion state of the moving tissue of interest;
forward projecting each of the plurality of groups of image data, generating a plurality of groups of forward projected data;
combining the plurality of groups of forward projected data;
determining update projection data based on a comparison between the combined plurality of groups of forward projected data and the measured projection data, wherein the measured projection data includes data detected over different motion states;
parsing the update projection data into a plurality of groups of update projection data, each group of update projection data corresponding to a different motion state of the moving tissue of interest;
back projecting each of the plurality of groups of updated projection data, generating a plurality of groups of update image data;
re-sampling each group of the plurality of groups of update image data to the reference motion state of the current image, wherein resampling each group of update image data to the reference motion state of the current image comprises applying a corresponding motion vector field of the set of motion vector fields to a corresponding each group of update image date that modifies the corresponding each group of update image data to the reference motion state of the current image; and
generating new current image data by combining the current image data and each group of re-sampled update image data.

2. The method of claim 1, further comprising:
repeating, at least one more time, all the acts of claim 1, but with the new current image data in place of the current image data.

3. The method of claim 1, further comprising:
outputting the new current image data as motion compensated iteratively reconstructed image data in response to satisfying stopping criteria.

4. The method of claim 3, wherein the stopping criteria is at least one of a predetermined number of iterations, a lapse of a predetermined amount of time, or a threshold on some discrepancy signal between the forward projected data and the measured projection data.

5. The method of claim 1, wherein combining the plurality of groups of forward projected data comprises:
concatenating the plurality of groups of forward projected data.

6. The method of claim 1, wherein combining the current image data and each of the groups of re-sampled update image data comprises:
adding each of the groups of re-sampled update image data to the current image data to generate the new current image data.

7. The method of claim 1, further comprising:
generating a set of motion vector fields, each motion vector field identifying a motion of tissue between the motion state of the current image data and a different motion state of the tissue of interest.

8. The method of claim 1, wherein the re-sampling of the current image data does not change a position, a shape or a size of any voxel as compared to a voxel grid of the current image data.

9. The method of claim 1, wherein the current image data is re-sampled into each of the plurality of groups of image data concurrently through parallel processing through a plurality of pre-forward projection re-sampling processing chains.

10. The method of claim 1, wherein the plurality of groups of image data are forward projected into the plurality of groups forward projection data concurrently through parallel processing through a plurality forward projection processing chains.

11. The method of claim 1, wherein the plurality of groups of update projection data are back projected into the plurality of different groups of update image data concurrently through parallel processing through a plurality of back projection processing chains.

12. The method of claim 1, wherein the plurality of groups of update image data are re-sampled into the plurality of groups of re-sampled update image data concurrently through parallel processing through a plurality post back projection re-sampling processing chains.

13. An imaging system, comprising:
a detector array that detects radiation emitted from a radiation source, and generates projection data indicative of the detected radiation, wherein the generated projection data includes data of and object moving over a range of motion states; and
a reconstructor comprising one or more processors configured to reconstruct volumetric image data at a reference state from the generated projection data over the range of motion states using a motion compensated iterative reconstruction algorithm in which forward projections and back projections are performed on re-sampled image volumes represented by voxels on a regular grid, wherein re-sampled image volumes comprises applied corresponding motion vector fields to image volume.

14. The imaging system of claim 13, wherein the reconstructor comprises:
a pre-forward projection re-sampler comprising the one or more processors configured to re-sample current image data into a plurality of groups of image data, each group of image data corresponding to a different motion state of moving tissue of interest;
a forward projector comprising the one or more processors configured to forward project each of the plurality of groups of image data, generating a plurality of groups of forward projected data, each group of forward projected data corresponding to a group of the plurality of groups of image data;

a forward projected data combiner comprising the one or more processors configured to combine the plurality of groups of forward projected data into forward projected data;

an update generator comprising the one or more processors configured to determine update projection data based on a comparison between the forward projected data and the generated projection data;

an update parser comprising the one or more processors configured to parse the update projected data into a plurality of groups of update projection data, each group of update projection data corresponding to a different motion state of the moving tissue of interest;

a back projector comprising the one or more processors configured to back project each of the plurality of groups of the update projection data, generating a plurality of groups of update image data;

a post-back projection re-sampler comprising the one or more processors configured to re-sample each group of plurality of groups of update image data to a motion state of the current image by applying a corresponding motion vector field; and an image updater comprising the one or more processors configured to update the current image data with the re-sample each group of the plurality of groups of update image data, generating new current image data.

15. The imaging system of claim 14,
the pre-forward projection re-sampler, comprising: a plurality of pre-forward projection re-sampling processing chains, wherein the pre-forward projection re-sampler concurrently re-samples the current image into the plurality of different groups of re-sampled image data through the plurality of the pre-forward projection re-sampling processing chains; and the forward projector, comprising: a plurality of forward projector processing chains, wherein the forward projector concurrently forward projects the plurality of different groups of re-sampled image data through the plurality of the forward projector processing chains.

16. The imaging system of claim 14,
the back projector, comprising: a plurality of back projector processing chains, wherein the back projector concurrently back projects the plurality of different groups of update projection data into the plurality of different groups of update image data through the plurality of the back projector processing chains, and the post-back projection re-sampler, comprising: a plurality of post-back projection re-sampling processing chains, wherein the post-back projection re-sampler concurrently re-samples the plurality of different groups of update image data through the plurality of the post-back projection re-sampling processing chains.

17. The imaging system of claim 14, further comprising:
wherein the forward projection data combiner combines the plurality of groups of forward projected data by concatenating the plurality of groups of forward projected data; and a comparator comprising the one or more processors configured to compare the concatenated plurality of groups of forward projected data with the generated projection data, generating a difference signal indicative of a comparison between the concatenated plurality of groups of forward projected data and the generated projection data, wherein the update generator determines the update projection data based on a difference signal.

18. The imaging system of claim 14, wherein the image updater updates the current image data by adding the re-sampled each group of the plurality of groups of update image data to the current image data.

19. The imaging system of claim 14, wherein the current image data and each of the groups of the plurality of groups of image data have a same geometric grid.

20. A non-transitory computer readable storage medium encoded with computer readable instructions, which, when executed by a processer, causes the processor to:

re-sample current image data into a plurality of groups of image data, each group of image data corresponding to different motion states of moving tissue of interest using a plurality of different motion vector fields that indicate a displacement of tissue in a reference state of the current image data to the corresponding different motion states;

forward project each group of the plurality of groups of image data, generating a plurality of groups of forward projected data, each group of forward projected data corresponding to a group of the plurality of groups of image data;

determine update projection data based on a comparison between the forward projected data and the measured projection data, wherein the measured projection data comprises data of a plurality of different motion states;

parse the update projection data into a plurality of groups of update projection data, each group of update projection data corresponding to a different motion state of the moving tissue of interest;

back project each of the plurality of groups of update projection data, generating a plurality of groups of update image data;

re-sample each group of update image data to the reference state of the current image, wherein each of the groups of re-sampled update image data includes data modified by a corresponding motion vector field;

generate new current image data by combining the current image data and each of the groups of re-sampled update image data; and repeat, at least one more iteration, all of the above acts, but with the new current image data in place of the current image data.

21. The non-transitory computer readable storage medium of claim 20, wherein the update projection data is a difference between the forward projected data and the measured projection data.

* * * * *